: US011981627B1

United States Patent
Ahmed et al.

(10) Patent No.: US 11,981,627 B1
(45) Date of Patent: May 14, 2024

(54) DISPERSIVE LIQUID-LIQUID MICROEXTRACTION OF COPPER AND ZINC IONS FROM REAL SAMPLES USING SELECTIVE ORGANOSELENIUM-BASED LIGANDS

(71) Applicant: KING FAISAL UNIVERSITY, Al-Ahsa (SA)

(72) Inventors: Hany Mohamed Abd El-Lateef Ahmed, Al-Ahsa (SA); Saadeldin Elsayed Ibrahim Shabaan, Al-Ahsa (SA); Mai Mustafa Khalaf Ali, Al-Ahsa (SA); Mohamed Gouda, Al-Ahsa (SA); Wael I. Mortada, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/244,933

(22) Filed: Sep. 12, 2023

Related U.S. Application Data

(62) Division of application No. 18/113,505, filed on Feb. 23, 2023, now Pat. No. 11,919,843.

(51) Int. Cl.
  *G01N 1/40* (2006.01)
  *C07C 391/02* (2006.01)
  *G01N 33/18* (2006.01)

(52) U.S. Cl.
  CPC ......... *C07C 391/02* (2013.01); *G01N 1/4044* (2013.01); *G01N 33/1813* (2013.01); *Y10T 436/107497* (2015.01); *Y10T 436/255* (2015.01)

(58) Field of Classification Search
  CPC ............... C07C 391/02; G01N 1/4044; G01N 33/1813; Y10T 436/107497; Y10T 436/255
  See application file for complete search history.

(56) References Cited

U.S. PATENT DOCUMENTS

2020/0281967 A1  9/2020  Arner et al.

OTHER PUBLICATIONS

Ma, H.-R. et al. "Studies on the acylation and condensation of 4-aminophenyl phenyl selenide," Chemical Journal of Chinese Universities 17(5) 727-730 (1996); including software translation (Year: 1996).*

Azooz, E.A. et al. "Green microextraction approach focuses on air-assisted dispersive liquid-liquid with solidified floating organic drop for preconcentration and determination of toxic metals in water and wastewater samples," Chemical Papers (2023) 77:3427-3438; Feb. 11, 2023 (Year: 2023).*

(Continued)

*Primary Examiner* — Jennifer Wecker
*Assistant Examiner* — Michelle Adams
(74) *Attorney, Agent, or Firm* — Nath, Goldberg & Meyer; Richard C. Litman

(57) ABSTRACT

Novel organoselenium selective ligands are presented and designed to determine metal ions in a sample. These ligands are used as complexing agents in a dispersive liquid-liquid microextraction procedure of copper and zinc ions. The procedure has a shortened extraction time, minimal organic solvent types, and lower amounts of solvents, as well as easy operation and high enrichment efficiency.

7 Claims, 3 Drawing Sheets

(56) References Cited

OTHER PUBLICATIONS

Wilson, J.G. et al. "Studies in negative ion mass spectrometry. V—A Comparison of positive a positive and negative ion mass spectra of copper(II) complexes of bidentate schiff base ligands," Organic Mass Spectrometry, 1975, vol. 10, pp. 1047 to 1057. (Year: 1975).*
Jungfer, M.R. et al. "Reactions of Schiff Base-Substituted Diselenides and -tellurides with Ni(II), Pd(II) and Pt(II) Phosphine Complexes," Eur. J. Inorg. Chem. 2020, 4303-4312 (Year: 2020).*
Pubchem Compound #159579293, Dec. 3, 2021.
Pubchem Compound #155559909, Feb. 17, 2021.

* cited by examiner

DISPERSIVE LIQUID-LIQUID MICROEXTRACTION OF COPPER AND ZINC IONS FROM REAL SAMPLES USING SELECTIVE ORGANOSELENIUM-BASED LIGANDS

CROSS-REFERENCE TO RELATED APPLICATION

This application is a divisional of U.S. patent application Ser. No. 18/113,505, filed on Feb. 23, 2023.

BACKGROUND

1. Field

The disclosure of the present patent application relates to novel organoselenium selective ligands to determine metal ions in a sample.

2. Description of the Related Art

Many analytical techniques are available for the determination of metal ions in a sample. However, the direct determination of such metal ions is typically limited due to the lack of sensitivity and matrix interference. Therefore, a preconcentration step is usually required prior to the analysis.

Recently, there is a trend for environmentally friendly separation procedures that use small amounts of organic solvents and agree with Green Chemistry Principles. Such procedures usually involve the chelation of metal ions by a suitable ligand to form a hydrophobic complex that is able to extract quantitatively in a micro-volume of the extracting solvent.

In general, not only natural amino acids but any organic acids bearing amino and/or hydroxy groups, preferably with these substituents in the alpha or beta position relative to the carboxyl unit, are generally suitable for preparing these metal chelates. However, preference is given to using the naturally occurring amino acids alanine, arginine (basic), asparaginne, aspartic acid (acidic), cysteine, glutamine, glutamic acid (acidic), glycine, histidine (basic), isoleucine, leucine, lysine (basic), methionine, phenylalanine, proline, serine, threonine, tryptophan, tyrosine and valine.

A suitable method for preparing such compounds, which are widely used, for example as additives in the human sector and in animal nutrition, is of great general interest. The chelate stability should not have an adverse effect on the bioavailability of the amino acid or hydroxycarboxylic acid. Many amino acid chelates even increase the bioavailability of the central cation coadministered compared to a salt or oxide of this cation.

According to the present-day state of the art, the production of suitable metal chelates as organic trace element compounds is mainly carried out with only low energy efficiency by wet chemical means or else by likewise energy-intensive mechanical processes with participation of milling media, especially in ball mills, within the latter case about 90% of the energy supplied being merely converted into heat (see EP 2489670 A1). The known wet-chemical processes are burdened by, in particular, the unavoidably energy-inefficient and correspondingly costly drying of the material; in addition, the product is not free of foreign inorganic anions.

Solvent-free processes, inter alia, are also known from the prior art (Rummel, U.S. Pat. No. 2,877,253 (A), 1959; Ashmead, Pedersen, U.S. Pat. No. 6,426,424 (B1), 2002; Pedersen, Ashmead, U.S. Pat. No. 6,518,240 (B1), 2003). Although solvent-free processes do not per se have the abovementioned disadvantage that large amounts of the solvent, normally water, must be removed, they do however require additional amounts of energy when product formation occurs in mechanical mills containing milling media, especially in ball mills. The reason for the increased energy consumption is that milling media must be set in motion as additional masses, for example in the process described by D. Ramhold, E. Gock, E. Mathies, W. Strauch, EP 2489670 (A1), 2012, in an excentric vibratory mill (EVM). When excentric vibratory mills are used, the energy consumption for driving the counterweight is additional. Furthermore, in such an inhomogeneously operating vibratory mill system, comparatively high wear is observed as a result of the high impact stresses on the milling media themselves. The abraded material is then undesirably found in the product.

In addition, the drying of material mentioned at the outset also becomes relevant in the last-named processes since water of reaction formed in this type of reaction milling has to be removed again under action of heat and/or with reduction of the pressure, with additional energy consumption.

A further disadvantage of the abovementioned solid-state processes for producing metal chelates is the sometimes considerable size heterogeneity and structural heterogeneity of the solid products obtained. Thus, for example, the process described in EP 2 489 670 A1 produces acicular metal-amino acid chelate structures having an average particle size of from 40 to 60 µm, with up to 80% of the particles having a particle size from >0 to 100 µm and up to 2% have a particle size of more than 500 µm, i.e. a value which is a factor of 10 higher than the "average size" of 50 µm, thus with a considerable amount of oversize particles.

A great structural heterogeneity quite generally increases the difficulty of further processing of the metal chelate complexes obtained, for example classification according to particle size, precise metering and homogeneous mixing with further substances. The active compound release kinetics are also unfavorably influenced by the particle size heterogeneity. A greatly acicular morphology hinders the flowability and scatterability of the particulate product. Acicular crystals of the complexes with are not readily water-soluble and sometimes even acid-insoluble can be hazardous to health when absorbed in the human or animal body. Acicular structures are therefore to be avoided.

Thus, new metal chelating complexes solving the aforementioned problems are desired.

SUMMARY

The present subject matter is directed to novel organoselenium selective ligands to determine metal ions in a sample.

In one embodiment, the present subject matter relates to an organoselenium compound having the formula I:

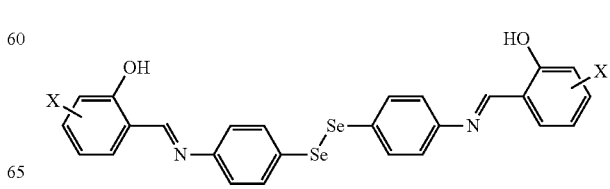

or an acceptable salt, ester, stereoisomer, or solvate thereof, wherein each X is the same and is hydrogen, fluorine, chlorine, bromine, cyano, —$NO_2$, $C_1$-$C_6$ alkyl, or $C_1$-$C_6$ alkoxy.

In another embodiment, the present subject matter relates to an organoselenium compound having the formula II:

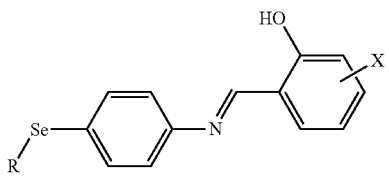

II or an acceptable salt, ester, stereoisomer, or solvate thereof, wherein X is hydrogen, fluorine, chlorine, bromine, cyano, —$NO_2$, $C_1$-$C_6$ alkyl, or $C_1$-$C_6$ alkoxy; and R is $C_1$-$C_6$ alkyl, phenyl, and $C_1$-$C_6$ alkylphenyl.

In a further embodiment, the present subject matter relates to an organoselenium compound having the formula III:

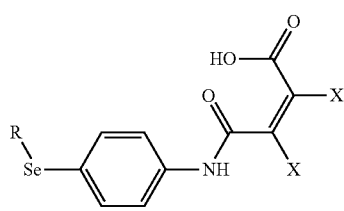

III or an acceptable salt, ester, stereoisomer, or solvate thereof, wherein each X is the same and is hydrogen, fluorine, chlorine, bromine, cyano, —$NO_2$, $C_1$-$C_6$ alkyl, or $C_1$-$C_6$ alkoxy; and R is $C_1$-$C_6$ alkyl, phenyl, and $C_1$-$C_6$ alkylphenyl.

Further contemplated herein are processes for making these organoselenium compounds, all comprising reacting a diselenide compound of the formula:

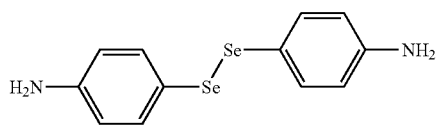

either directly or indirectly with a substituted salicylaldehyde of the formula:

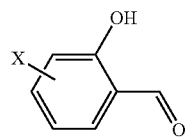

in the presence of ethanol and acetic acid, or with a toluene of the formula:

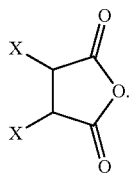

Also contemplated herein are methods for determining metal ions in a sample, the method comprising: complexing the organoselenium compounds as described herein with metal ions in the sample to obtain a complex; and extracting the complex in a small volume of an alcohol.

These and other features of the present subject matter will become readily apparent upon further review of the following specification.

DETAILED DESCRIPTION OF THE PREFERRED EMBODIMENTS

Figure 1:
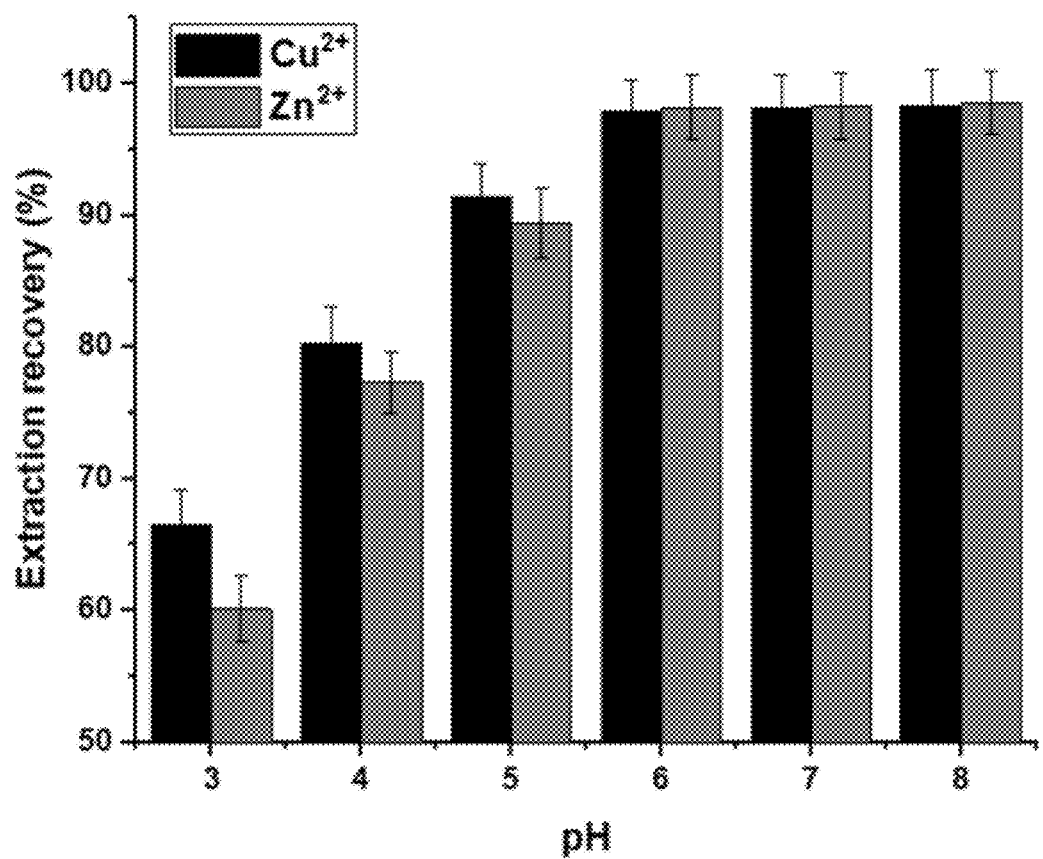
FIG. 1 is a chart showing the effect of pH on extraction recovery of $Cu^{2+}$ and $Zn^{2+}$.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino.

The term "substituted alkenyl" refers to an alkenyl group in which 1 or more (up to about 5, for example about 3) hydrogen atoms is replaced by a substituent independently selected from those listed above with respect to a substituted alkyl.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Compounds

In one embodiment, the present subject matter relates to an organoselenium compound having the formula I:

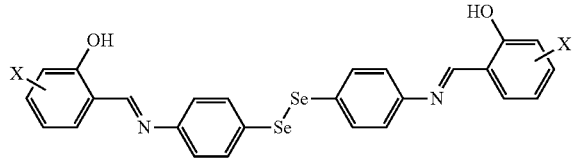

I or an acceptable salt, ester, stereoisomer, or solvate thereof, wherein each X is the same and is hydrogen, fluorine, chlorine, bromine, cyano, —$NO_2$, $C_1$-$C_6$ alkyl, or $C_1$-$C_6$ alkoxy.

In one embodiment, the present subject matter relates to a compound of formula I, wherein each X, which is the same, is at the 3-position of its respective phenyl ring.

In another embodiment, the present subject matter relates to a compound of formula I, wherein each X, which is the same, is hydrogen, fluorine, chlorine, bromine, cyano, —$NO_2$, methyl, or methoxy.

In still another embodiment, the present subject matter relates to a compound of formula I, wherein each X, which is the same, is hydrogen, 3-fluorine, 3-chlorine, 3-bromine, 3-cyano, 3-$NO_2$, 3-methyl, or 3-methoxy.

In a further embodiment, the present subject matter relates to a compound of formula I, wherein the compound is selected from the group consisting of

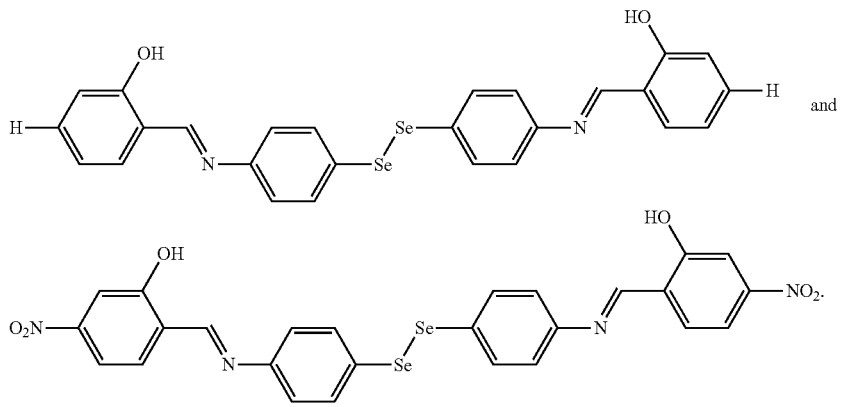

In another embodiment, the present subject matter relates to an organoselenium compound having the formula II:

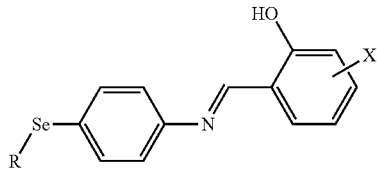

II or an acceptable salt, ester, stereoisomer, or solvate thereof, wherein X is hydrogen, fluorine, chlorine, bromine, cyano, —$NO_2$, $C_1$-$C_6$ alkyl, or $C_1$-$C_6$ alkoxy; and R is $C_1$-$C_6$ alkyl, phenyl, and $C_1$-$C_6$ alkylphenyl.

In one embodiment, the present subject matter relates to a compound of formula II, wherein X is at the 3-position of its respective phenyl ring.

In another embodiment, the present subject matter relates to a compound of formula II, wherein X is hydrogen, fluorine, chlorine, bromine, cyano, —$NO_2$, methyl, or methoxy.

In still another embodiment, the present subject matter relates a compound of formula II, wherein X is hydrogen, 3-fluorine, 3-chlorine, 3-bromine, 3-cyano, 3-$NO_2$, 3-methyl, or 3-methoxy.

In still yet another embodiment, the present subject matter relates a compound of formula II, wherein R is ethyl, propyl, butyl, phenyl, or ethylphenyl.

In a further embodiment, the present subject matter relates to a compound of formula II, wherein the compound is selected from the group consisting of

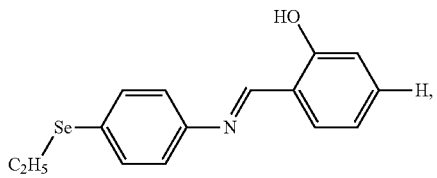

and

-continued

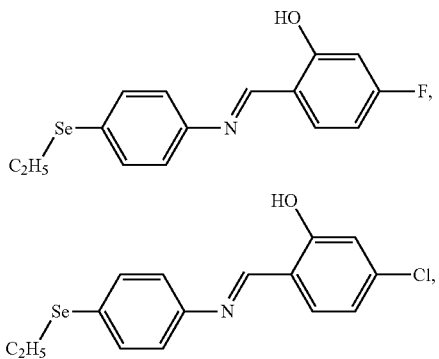

-continued

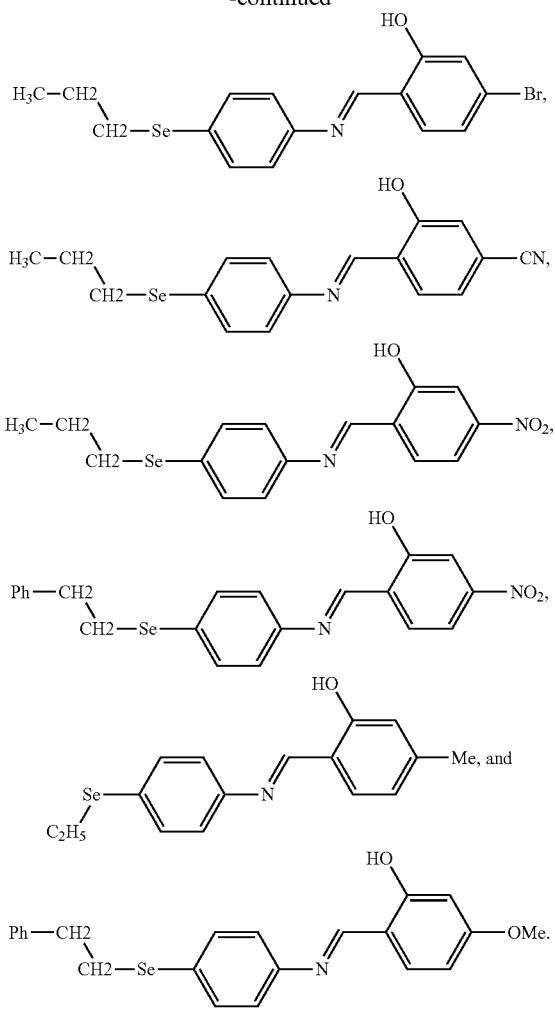

In a further embodiment, the present subject matter relates to an organoselenium compound having the formula III:

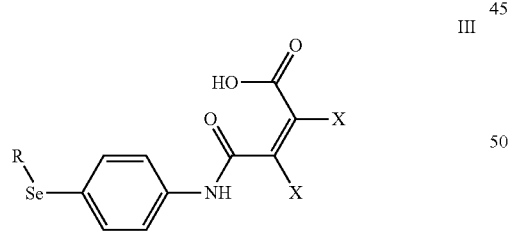

or an acceptable salt, ester, stereoisomer, or solvate thereof, wherein each X is the same and is hydrogen, fluorine, chlorine, bromine, cyano, —NO$_2$, C$_1$-C$_6$ alkyl, or C$_1$-C$_6$ alkoxy; and R is C$_1$-C$_6$alkyl, phenyl, and C$_1$-C$_6$ alkylphenyl.

In another embodiment, the present subject matter relates to a compound of formula III, wherein each X, which is the same, is hydrogen, fluorine, chlorine, bromine, cyano, —NO$_2$, methyl, or methoxy.

Accordingly, in certain embodiments, when each X is hydrogen, the present subject matter relates to a compound of formula IIIA:

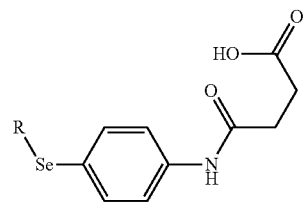

or an acceptable salt, ester, stereoisomer, or solvate thereof, wherein R is C$_1$-C$_6$ alkyl, phenyl, and C$_1$-C$_6$ alkylphenyl.

In still yet another embodiment, the present subject matter relates a compound of formula III, wherein R is ethyl, propyl, butyl, phenyl, or ethylphenyl.

In a further embodiment, the present subject matter relates to a compound of formula III, wherein the compound is selected from the group consisting of

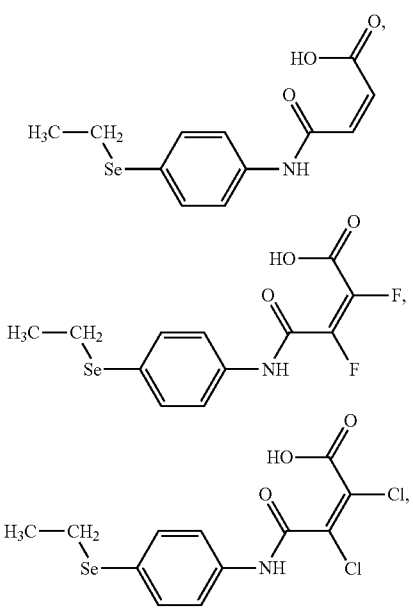

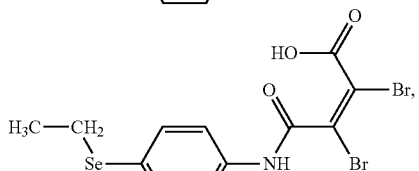

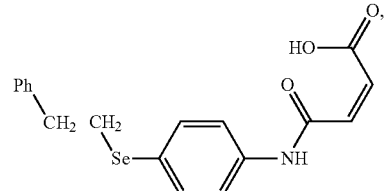

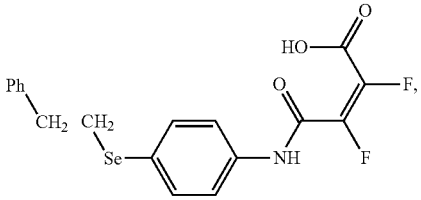

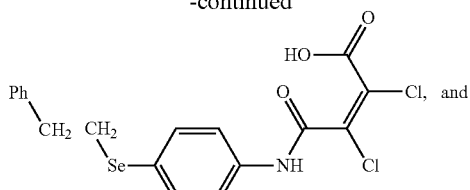

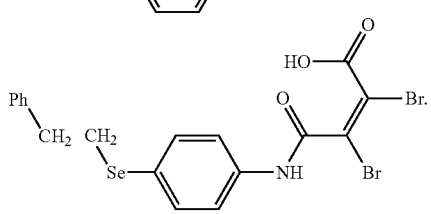

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phos-phates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g. when isolated in crystalline form, varying amounts of solvents. Included within the present scope are, therefore, all solvates of the present compounds, as well as the solvates of the salts, the stereoisomers and the salts of the stereoisomers of the present compounds.

The present compounds may be isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the present compounds and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, unacceptable salts, which can be obtained, for example, as process products in the manufacturing on an industrial scale, can be converted into acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

Processes of Making the Compounds

Further contemplated herein are processes for making these organoselenium compounds, all comprising reacting a diselenide compound of the formula:

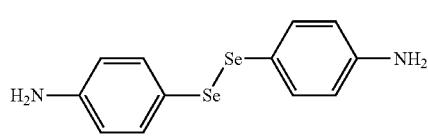 [SMILES: Nc1ccc([Se][Se]c2ccc(N)cc2)cc1]

either directly or indirectly with a substituted salicylaldehyde of the formula:

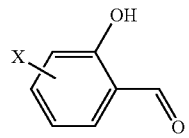

In this regard, the compounds of formula I can be made by directly reacting the diselenide compound shown above with the substituted salicylaldehyde in the presence of ethanol and acetic acid. In one embodiment in this regard, the acetic acid is added as drops to the reaction mixture.

Accordingly, one embodiment of the present subject matter relates to a process for making the organoselenium compound of formula I, comprising reacting a diselenide compound of the formula:

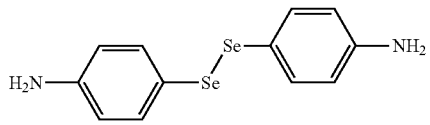

with a substituted salicylaldehyde of the formula:

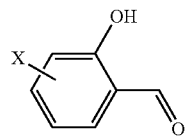

in the presence of ethanol and acetic acid. This reaction can be seen by referring to Scheme I:

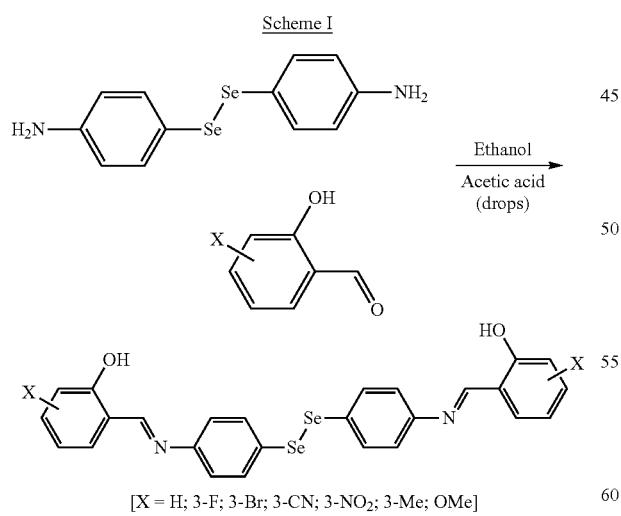

Further, the compounds of formula II can be made by indirectly reacting the diselenide compound shown above with the substituted salicylaldehyde in the presence of ethanol and acetic acid. That is, the diselenide undergoes a first reaction, with the resultant product of that first reaction being further reacted with the substituted salicylaldehyde in the presence of ethanol and acetic acid. In one embodiment in this regard, the acetic acid is added as drops to this second reaction mixture.

Accordingly, one embodiment of the present subject matter relates to a process for making the organoselenium compound of formula II, comprising reacting a diselenide compound of the formula:

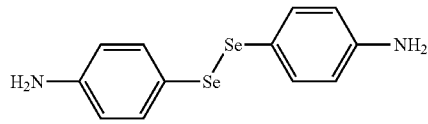

with R—Br in the presence of ethanol $NaBH_4$, and $N_2$ to obtain a compound of the formula:

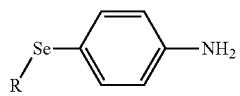

which compound in turn is reacted with a substituted salicylaldehyde of the formula:

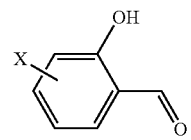

in the presence of ethanol and acetic acid. This reaction can be seen by referring to Scheme II:

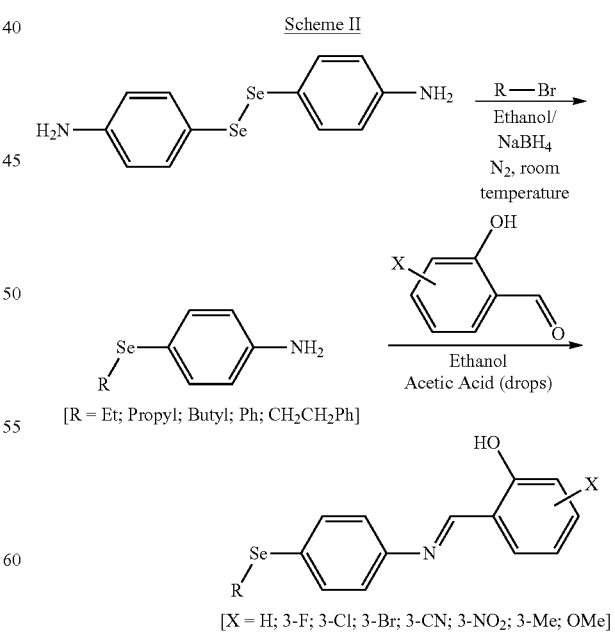

Likewise, the compounds of formula III can be made by indirectly reacting the diselenide compound shown above with toluene. That is, the diselenide undergoes a first reaction, with the resultant product of that first reaction being further reacted with the toluene.

Accordingly, one embodiment of the present subject matter relates to a process for making the organoselenium compound of formula III, comprising reacting a diselenide compound of the formula:

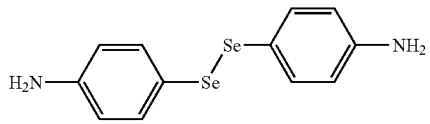

with R—Br in the presence of ethanol, NaBH$_4$, and N$_2$ to obtain a compound of the formula:

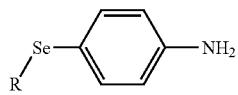

which compound in turn is reacted with a toluene of the formula:

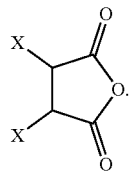

This reaction can be seen by referring to Schemes III and IV:

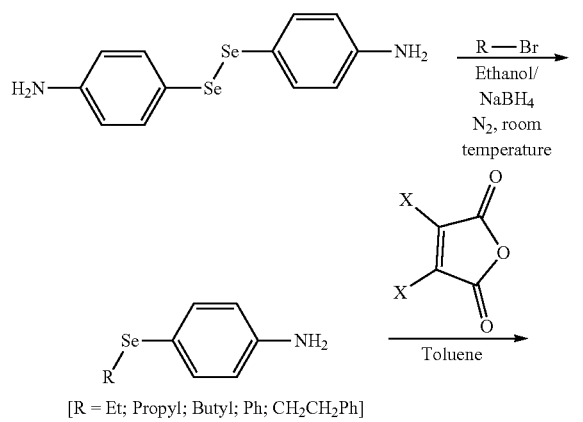

Scheme III

[R = Et; Propyl; Butyl; Ph; CH$_2$CH$_2$Ph]

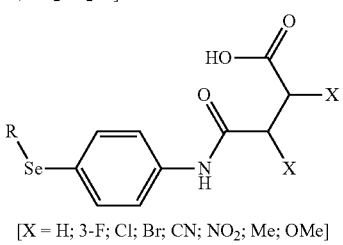

[X = H; 3-F; Cl; Br; CN; NO$_2$; Me; OMe]

Scheme IV

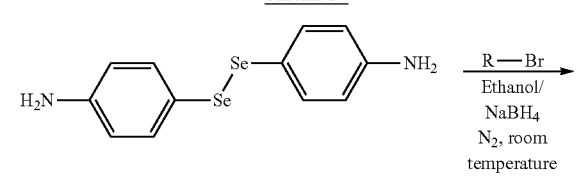

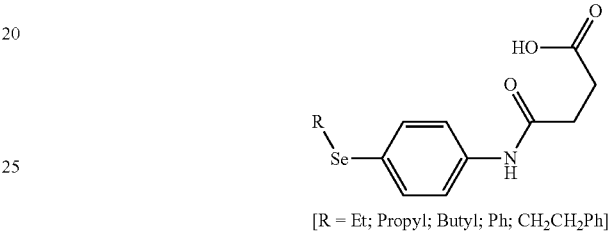

[R = Et; Propyl; Butyl; Ph; CH$_2$CH$_2$Ph]

Methods of Use

The present organoselenium compounds have valuable properties, which make them commercially utilizable. In particular, the present organoselenium compounds are selective ligands that can be used as complexing agents in the dispersive liquid-liquid microextraction procedure of metals including, by way of non-liming example, copper and zinc ions. The extraction procedures using the present compounds can result in a shortened extraction time, the use of minimal organic solvent types, lower amount of solvents being used, as well as easy operation and high enrichment efficiency. Further, the present compounds represent an improvement over other reported organic ligands used in liquid-liquid micro-extraction methods, as the present compounds have higher chemical and thermal stability and are less toxic, making them safer to use.

In this regard, the thermal stability of the present compounds was confirmed by determining their higher melting point and higher decomposition points to be about 150 to about 200° C. The present compounds were likely confirmed to be less toxic by using them in a MTT assay against HepG2 and MCF-7 cancer cells as well as normal WI-38 cell lines. Most of the compounds did not show any toxicity at the employed concentration range.

In one embodiment, the target metals, such as copper (Cu$^{2+}$) and zinc (Zn$^{2+}$) ions are complexed with the organoselenium compounds. This complexation can occur at a pH of about 4.0 to about 6.0, about 5.0, or about 4.0, about 4.5, about 5.0, about 5.5, or about 6.0, followed by extraction into a small volume of an alcohol including, by way of non-limiting example, 1-undecanol.

In one embodiment in this regard, the present subject matter relates to a method for determining metal ions in a sample, the method comprising: complexing the organoselenium compound as described herein with metal ions in the sample to obtain a complex; and extracting the complex in a small volume of an alcohol. In one embodiment in this regard, the metal ions are selected from the group consisting of zinc ions, copper ions, and a combination thereof, and the alcohol is 1-undecanol.

Once the complex is extracted, phase separation can be achieved by centrifugation and the floated organic drop can be solidified by cooling in an ice bath. The solidified drop that contains the analytes can be transported to another tube and diluted with 0.5 mL $HNO_3$ (1.0 molar) prior to aspiration into flame atomic absorption spectrometry.

In use, the present organoselenium ligands have selective chelating efficiency for the copper and zinc ions with low detection limits (less than 1.0 µg $L^{-1}$). Further, at the optimum conditions (pH 6.0, 0.1 mmol/L of Ligand, 75 µL of 1-undecanol), the calibration curves are linear up to 1000 µg $L^{-1}$.

Figure 2:
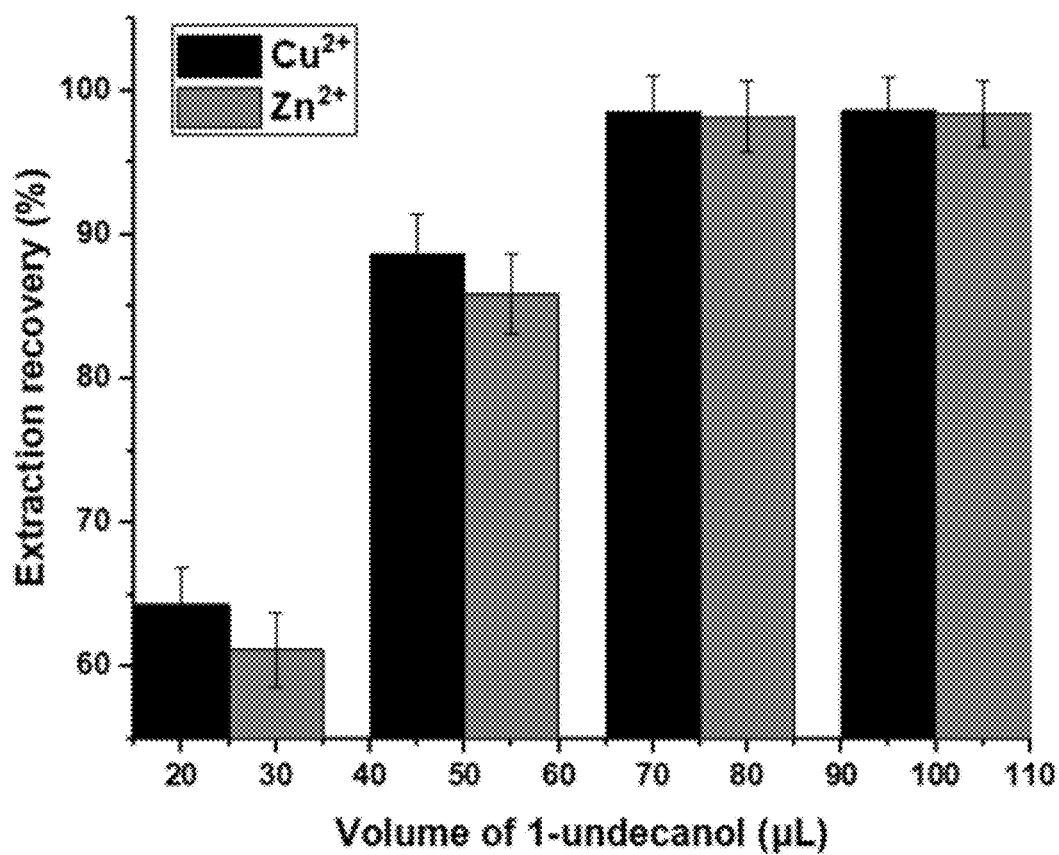
FIG. 2 is a chart showing the effect of 1-undecanol volume on the extraction recovery of $Cu^{2+}$ and $Zn^{2+}$.
Figure 3:
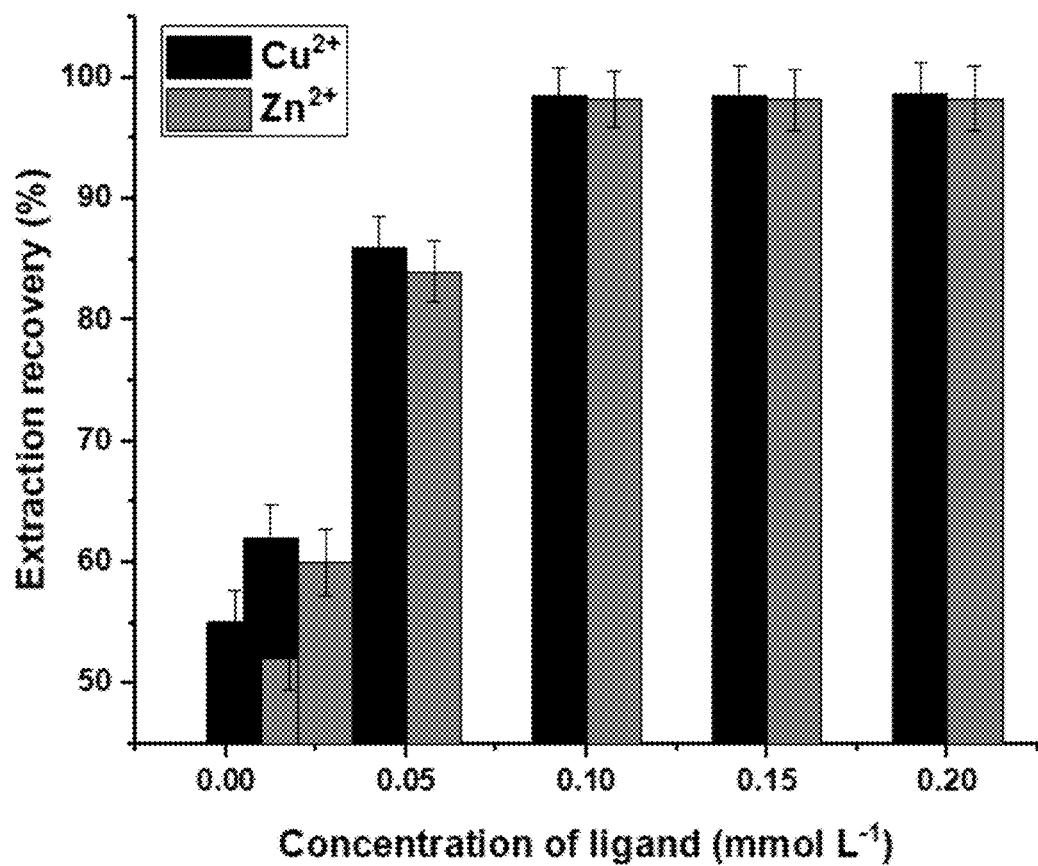
FIG. 3 is a chart showing the effect of ligand concentration on the extraction recovery of $Cu^{2+}$ and $Zn^{2+}$.

FIGS. 1-3 show the effect of pH, 1-undecanol, and concentration of ligand on the extraction recoveries of $Cu^{2+}$ and $Zn^{2+}$, respectively. Under these conditions, the linear dynamic range was up to 1000 µg $L^{-1}$ for both ions with regression equations of Intensity (ICP-OES)=0.0313 $[Cu^{2+}]$–0.004 and Intensity=0.0221 $[Zn^{2+}]$–0.009, respectively, where [Cu] and [Zn] were the concentrations in µg $L^{-1}$.

It is to be understood that the organoselenium compounds are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method for determining metal ions in a sample, the method comprising:
    complexing an organoselenium compound with a metal ion in the sample to obtain a complex; and
    extracting the complex in a volume of an alcohol;
    wherein the organoselenium compound has the formula I:

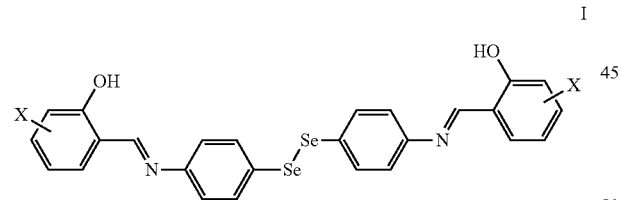

or a salt, stereoisomer, or solvate thereof, and
    wherein each X is the same and is hydrogen, fluorine, chlorine, bromine, cyano, —$NO_2$, $C_1$-$C_6$ alkyl, or $C_1$-$C_6$ alkoxy.

2. The method of claim 1, wherein the sample comprises metal ions selected from the group consisting of zinc ions, copper ions, and a combination thereof, and the alcohol is 1-undecanol.

3. The method for determining metal ions in a sample of claim 1, wherein each X is hydrogen, flourine, chlorine, bromine, cyano, —$NO_2$, methyl, or methoxy.

4. A method for determining metal ions in a sample, the method comprising:
    complexing an organoselenium compound with a metal ion in the sample to obtain a complex; and
    extracting the complex in a volume of an alcohol;
    wherein the organoselenium compound has the formula II:

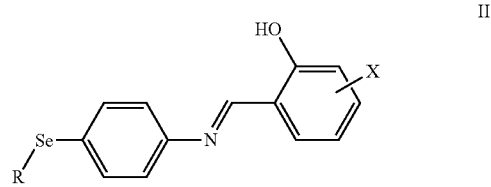

or a salt, stereoisomer, or solvate thereof,
    wherein X is hydrogen, fluorine, chlorine, bromine, cyano, —$NO_2$, $C_1$-$C_6$ alkyl, or $C_1$-$C_6$ alkoxy; and R is $C_1$-$C_6$ alkyl, phenyl, or $C_1$-$C_6$ alkylphenyl.

5. The method of claim 4, wherein the sample comprises metal ions selected from the group consisting of zinc ions, copper ions, and a combination thereof, and the alcohol is 1-undecanol.

6. The method for determining metal ions in a sample of claim 4, wherein X is hydrogen, fluorine, chlorine, bromine, cyano, $NO_2$, methyl, or methoxy; and R is ethyl, propyl, butyl, phenyl, or ethylphenyl.

7. The method for determining metal ions in a sample of claim 4, wherein the organoselenium compound is selected from the group consisting of:

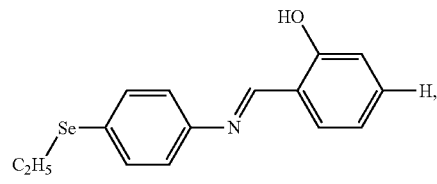

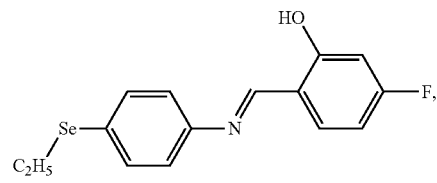

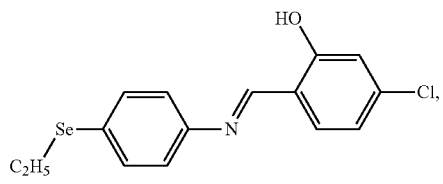

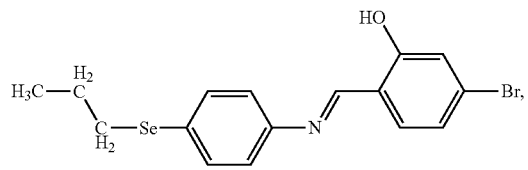

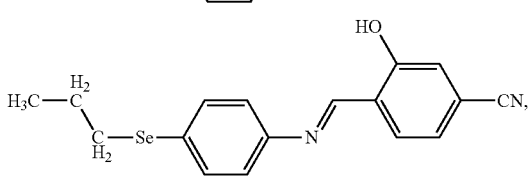

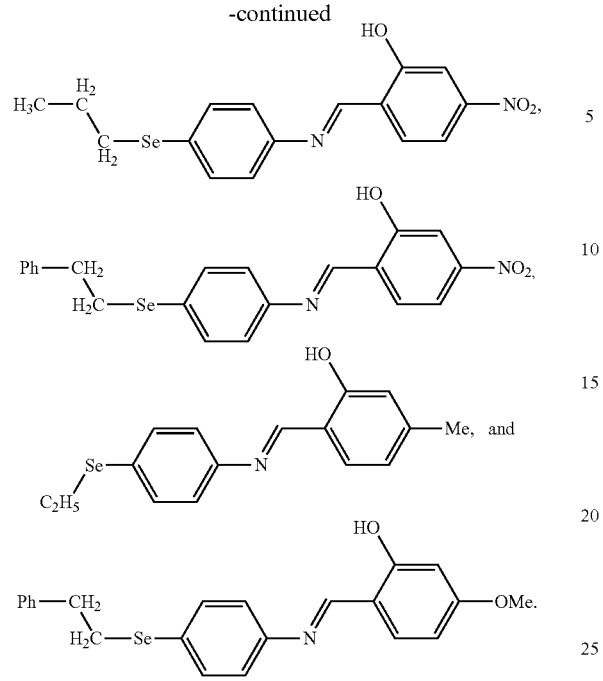
* * * * *